(12) United States Patent
Herrala et al.

(10) Patent No.: US 10,357,170 B2
(45) Date of Patent: Jul. 23, 2019

(54) METHOD AND A DEVICE FOR MEASURING MUSCLE SIGNALS

(75) Inventors: Mika Herrala, Vimpeli (FI); Pasi Tavi, Kuopio (FI); Jani Mäntyjärvi, Oulunsalo (FI); Mikko Vähäsöyrinki, Oulu (FI)

(73) Assignee: FIBRUX OY, Vimpeli (FI)

( * ) Notice: Subject to any disclaimer, the term of this patent is extended or adjusted under 35 U.S.C. 154(b) by 1009 days.

(21) Appl. No.: 13/881,827

(22) PCT Filed: Oct. 28, 2011

(86) PCT No.: PCT/FI2011/050946
§ 371 (c)(1),
(2), (4) Date: May 31, 2013

(87) PCT Pub. No.: WO2012/056114
PCT Pub. Date: May 3, 2012

(65) Prior Publication Data
US 2013/0261423 A1    Oct. 3, 2013

(30) Foreign Application Priority Data

Oct. 29, 2010  (FI) ...................................... 20106134

(51) Int. Cl.
*A61B 5/04*      (2006.01)
*A61B 5/0488*    (2006.01)
*A61B 5/0492*    (2006.01)

(52) U.S. Cl.
CPC ........ *A61B 5/04014* (2013.01); *A61B 5/0488* (2013.01); *A61B 5/0492* (2013.01)

(58) Field of Classification Search
CPC .. A61B 5/04014; A61B 5/0492; A61B 5/0488
See application file for complete search history.

(56) References Cited

U.S. PATENT DOCUMENTS 5,058,602 A * 10/1991 Brody ................. A61B 5/0488
                                                600/546
5,318,039 A *  6/1994 Kadefors ............ A61B 5/0488
                                                600/546

(Continued)

FOREIGN PATENT DOCUMENTS

EP       2057943 A1      5/2009
WO    WO 91/01683 A1     2/1991
WO    WO 2010/038178  *  4/2010

OTHER PUBLICATIONS

Spectral moments of mechanomyographic signals recorded with accelerometer and microphone during sustained fatiguing contractions, Madeleine et al., Med Biol Eng Comput (2006) 44: 290-297.*

(Continued)

*Primary Examiner* — Rene T Towa
(74) *Attorney, Agent, or Firm* — Ziegler IP Law Group, LLC (57) ABSTRACT

A method, system and apparatus for determining the state of a muscle between a normal non-tired state, a tired state and a passive involuntary tension state. A signal from the muscle is recorded at rest by using an electrode arrangement, where an earth body may prevent the electrodes from picking up signals beyond the extent of the earth body. The frequency content of the signal is determined by spectral analysis, e.g. by computing a moment of the spectrum. A normal frequency content indicates a non-tired muscle state, whereas a low and a high frequency content indicate a tired and a passive involuntary tension muscle state.

16 Claims, 6 Drawing Sheets

(56) References Cited

U.S. PATENT DOCUMENTS

| | | | |
|---|---|---|---|
| 5,349,963 A | 9/1994 | Eskelinen | |
| 5,361,775 A * | 11/1994 | Remes | A61B 5/04012 |
| | | | 600/546 |
| 5,645,073 A * | 7/1997 | Kadefors | A61B 5/0488 |
| | | | 600/546 |
| 5,671,752 A * | 9/1997 | Sinderby | A61B 5/04884 |
| | | | 600/546 |
| 5,693,000 A * | 12/1997 | Crosby | A61N 1/36042 |
| | | | 600/16 |
| 2002/0156399 A1 * | 10/2002 | Kanderian | A61B 5/0488 |
| | | | 600/587 |
| 2003/0109905 A1 * | 6/2003 | Mok | A61B 5/0002 |
| | | | 607/60 |
| 2004/0082877 A1 * | 4/2004 | Kouou | A61B 5/0488 |
| | | | 600/546 |
| 2004/0225211 A1 * | 11/2004 | Gozani | A61B 5/04004 |
| | | | 600/382 |
| 2005/0049517 A1 | 3/2005 | Mathew | |
| 2005/0080828 A1 * | 4/2005 | Johnson | A61B 5/048 |
| | | | 708/160 |
| 2006/0025666 A1 | 2/2006 | Getsla | |
| 2006/0161225 A1 * | 7/2006 | Sormann | A61B 5/0031 |
| | | | 607/61 |
| 2006/0183980 A1 * | 8/2006 | Yang | A61B 5/6804 |
| | | | 600/301 |
| 2007/0249957 A1 * | 10/2007 | Gentempo | A61B 5/0488 |
| | | | 600/546 |
| 2007/0276282 A1 * | 11/2007 | Fukumura | A61B 5/04012 |
| | | | 600/546 |
| 2008/0001735 A1 * | 1/2008 | Tran | G06F 19/3418 |
| | | | 340/539.22 |
| 2008/0082137 A1 * | 4/2008 | Kieval | A61N 1/0551 |
| | | | 607/30 |

OTHER PUBLICATIONS

Tetsurou Torisu, Effects of muscle fatigue induced by low-level clenching on experimental muscle pain and resting jaw muscle activity: gender differences, Research Article, Accepted: Apr. 6, 2006/ Published online: May 6, 2006 © Springer-Verlag 2006.

PCT International Report on Patentability, dated Jan. 9, 2013.

Sparto, Patrick J., et al., "Wavelet and Short-Time Fourier Transform Analysis of Electromyography for Detection of Back Muscle Fatigue", IEEE Transactions on Rehabilitation Engineering, vol. 8, No. 3, Sep. 2000, pp. 433-436.

Kwatny, Eugene, et al., "An Application of Signal Processing Techniques to the Study of Myoelectric Signals", IEEE Transactions on Biomedical Engineering, vol. BME-17, No. 4, Oct. 1, 1970, pp. 303-313.

Karagozoglu, Bahattin, et al., "Design and Development of a Practical Muscle Fatigue Monitor", 5th IEEE GCC & Exhibition, Mar. 17-19, 2009, 7 pages.

Extended European Search Report for European Patent Application No. EP11835697.1, dated Jun. 26, 2017, 10 pages.

Communication Pursuant to Article 94(3) EPC for European Patent Application No. EP11835697.1, dated Sep. 21, 2018, 11 pages.

\* cited by examiner

Fig. 6b

METHOD AND A DEVICE FOR MEASURING MUSCLE SIGNALS

FIELD OF THE INVENTION

The present invention relates to a method, a device, a system and a computer program product for measuring muscle signals. More specifically, the present invention relates to the detection of the state and the properties of the muscle and a device, system and a computer program product for the same.

BACKGROUND OF THE INVENTION

Human skeletal muscles consist of a large number of motor units that are bundles of muscle cells acting in synchrony and excited by the same neuronal signal. The electrical excitation of the muscle causes the muscle to contract and carry out work. The electrical excitation in the muscle can be measured as a voltage between two electrodes in the tissue or on the skin. The operation of the muscle may be analyzed from the characteristics of this signal picked up by the electrodes. The properties of the voltage signal depend on the total activity of the muscle and on the relative activity of the different types of activated motor units within the given muscle.

The strength and endurance of muscles may be developed by planned exercise. To improve performance in sports, the muscles need to be exercised so that they get tired, but so that the muscles still recover from the exercise reasonably quickly. Also, there are many contemporary professions that tend to encourage a person to stay in the same position for a long time. This also causes the muscles to get tired.

With state of the art methods and devices for analyzing the operation of muscles, it has proven to be difficult to determine when a muscle is tired to an extent that it still recovers reasonably quickly, and when the muscle is tired to an extent that recovery takes significantly longer.

There is, therefore, a need for a solution that enables a more accurate and reliable analysis of muscle signals for determining the tiredness of the muscle for example for guiding a sports exercise.

SUMMARY OF THE INVENTION

Now there has been invented an improved method and technical equipment implementing the method, by which the above problems are alleviated. Various aspects of the invention include a method, an apparatus, a system and a computer readable medium comprising a computer program stored therein, which are characterized by what is stated in the independent claims. Various embodiments of the invention are disclosed in the dependent claims.

The invention relates to determining the state of a muscle between a normal (non-tired, fresh) state, a tired (fatigued) state and a passive involuntary tense (PIT) state. The invention also relates to determining the properties of the muscle e.g. related to the relative proportions of different types of motor units in the given muscle. The embodiments may also be applicable to the detection of muscle properties in certain states such as multiple sclerosis (MS), myalgia or Parkinson's disease. A signal from the muscle is recorded at rest (and/or during muscle activity) by using an electrode arrangement, where an earth body may prevent the electrodes from picking up signals beyond the extent of the earth body. The frequency content of the signal is determined by spectral analysis, e.g. by computing a moment of the spectrum. In a resting muscle, a normal frequency content indicates a normal non-tired muscle state, whereas a low and a high frequency content indicate a tired and a passive involuntary tension state. In other words, if the signal coming from the muscle contains an unusually high amount of high frequencies, a passive involuntary tension muscle state is determined. A tired muscle may be returned to the normal state by rest and recovery from exercise, and a passive involuntary tension state may be returned to normal state by stretching or massage. In activated muscle, the frequency content of the spectrum depends on the relative amount of different types of activated motor units. The higher is the force the muscle is producing, the higher is the frequency of the activation.

According to a first aspect of the invention, there is provided a method for analyzing muscle signals, the method comprising receiving a signal, the signal having been measured from a muscle in a resting state using an electrode, determining a measure indicative of frequency content of said signal, determining a measure indicative of strength of said signal in a high frequency, wherein said high frequency essentially corresponds to frequencies produced by a muscle (e.g. at rest) in a passive involuntary tension state, and wherein said high frequency is higher in frequency than a normal frequency, wherein said normal frequency essentially corresponds to frequencies produced by a muscle (e.g. at rest) in a non-tired state, and determining that a muscle is in a passive involuntary tension state based on said measure indicative of strength of said signal in a high frequency. According to an embodiment, the signal may be acquired from voluntary or involuntary activated muscles and the frequency properties of the signal may be used to estimate the properties and the components of the muscle.

According to an embodiment, the method comprises acquiring a signal from a muscle (e.g. at rest) with a number (e.g. at least two) electrodes placed on the skin on top of said muscle, determining a moment value of a spectrum of said signal, wherein said moment is indicative of a measure determined or determinable by multiplying a frequency value of a frequency bin with an amplitude value of the same bin to form a bin product and summing bin products for different frequencies, wherein said moment value corresponds to frequency content of said signal, determining whether said moment has a normal value, a low value or a high value, corresponding to a normal, low and high frequency content of said signal, determining that a muscle is in a non-tired state if said moment has a normal value, determining that a muscle is in a tired state if said moment has a low value, determining that a muscle is in a passive involuntary tension state if said moment has a high value, and guiding an exercise using said determined state of said muscle.

According to a second aspect of the invention, there is provided an electrode arrangement for use in a muscle state analyzer comprising at least two electrodes of conducting material arranged to make contact with the skin when said electrode arrangement is operated, an electrical insulator surrounding at least one of said at least two electrodes, and a passive earth body of a conducting material arranged to make contact with the skin when said electrode arrangement is operated, said earth body surrounding said at least two electrodes to limit said at least two electrodes from picking up a signal from outside of the extent of said earth body.

According to an embodiment, the electrode arrangement comprises at least two pairs of electrodes, said at least two pairs of electrodes having a different distance between the electrodes in the pair for creating a different depth sensitivity for the said at least two pairs of electrodes. According to an embodiment, the at least two pairs of electrodes are arranged in either a linear arrangement essentially along one line or in a crossed setting such as the lines between electrodes in the electrode pairs forming a straight angle cross.

According to a third aspect of the invention, there is provided an apparatus for determining the state of a muscle, comprising a processor, memory including computer program code, the memory and the computer program code configured to, with the processor, cause the apparatus to receive a signal, the signal having been measured from a muscle in a resting state using an electrode, determine a measure indicative of frequency content of said signal, determine a measure indicative of strength of said signal in a high frequency, wherein said high frequency essentially corresponds to frequencies produced by a muscle (e.g. at rest) in a passive unvoluntary tension state, and wherein said high frequency is higher in frequency than a normal frequency, wherein said normal frequency essentially corresponds to frequencies produced by a muscle (e.g. at rest) in a non-tired state, and determine that a muscle is in a passive involuntary tension state based on said measure indicative of the strength of said signal in a high frequency.

According to an embodiment, the apparatus comprises a unit for processing said signal measured from a muscle, an electrode arrangement according to the second aspect and embodiments of the invention, and an indicator for indicating that a muscle is in a passive involuntary tension state based on said measure indicative of the strength of said signal in a high frequency. According to an embodiment, the apparatus comprises computer program code configured to, with the processor, cause the apparatus to acquire a signal from a muscle (e.g. at rest) with at least two electrodes placed on the skin on top of said muscle, determine a moment value of a spectrum of said signal, wherein said moment is indicative of a measure determined or determinable by multiplying a frequency value of a frequency bin with an amplitude value of the same bin to form a bin product and summing bin products for different frequencies, wherein said moment value corresponds to frequency content of said signal, determine whether said moment has a normal value, a low value or a high value, corresponding to a normal, low and high frequency content of said signal, determine that a muscle is in a non-tired state if said moment has a normal value, determine that a muscle is in a tired state if said moment has a low value, and determine that a muscle is in a passive involuntary tension state if said moment has a high value.

According to a fourth aspect of the invention, there is provided a system for determining the state of a muscle, comprising an electrode arrangement, a processor, memory including computer program code, the memory and the computer program code configured to, with the processor, cause the system to acquire a signal from a muscle (e.g. at rest) with at least two electrodes in said electrode arrangement, determine a measure indicative of frequency content of said signal, determine a measure indicative of strength of said signal in a high frequency, wherein said high frequency essentially corresponds to frequencies produced by a muscle (e.g. at rest) in a passive involuntary tension state, and wherein said high frequency is higher in frequency than a normal frequency, wherein said normal frequency essentially corresponds to frequencies produced by a muscle (e.g. at rest) in a non-tired state, and determine that a muscle is in a passive involuntary tension state based on said strength of said signal in a high frequency. The system may comprise an electrode unit, an acquisition unit, an analysis unit and an indicator unit embodied in one or more housings and/or operatively connected with each other.

According to a fifth aspect of the invention, there is provided a computer program product embodied on a non-transitory computer readable medium, the computer program product comprising computer instructions that, when executed on at least one processor of a system, cause the system to receive a signal, the signal having been measured from a muscle in a resting state using an electrode, determine a frequency content of said signal, determine a strength of said signal in a high frequency, wherein said high frequency essentially corresponds to frequencies produced by a muscle (e.g. at rest) in a passive involuntary tension state, and wherein said high frequency is higher in frequency than a normal frequency, wherein said normal frequency essentially corresponds to frequencies produced by a muscle (e.g. at rest) in a non-tired state, and determine that a muscle is in a passive involuntary tension state based on said strength of said signal in a high frequency.

DESCRIPTION OF THE DRAWINGS

In the following, various embodiments of the invention will be described in more detail with reference to the appended drawings, in which.

DESCRIPTION OF EXAMPLE EMBODIMENTS

In the following, several embodiments of the invention will be described in the context of a system for analyzing muscle signals to determine the tiredness of a muscle. It is to be noted, however, that the invention is not limited to this type of muscle analysis only. In fact, the different embodiments may have applications widely in any environment where recording and analysis of bioelectric signals is required.

The invention may have applications in planning and carrying out exercise of muscles for humans and animals, and it may also have applications in detecting and controlling the tiredness of muscles for any practical purpose. To this end, various devices, systems and arrangements are presented and claimed in the attached claims. These devices, systems and arrangements may have applications in private use for detecting tiredness of muscles, e.g. to help exercise a sport or to predict and/or prevent excessive tiredness of muscles for any purpose. These devices, systems and arrangements may be also be used as an element in maintaining muscles in a good condition e.g. for the purposes or occupational health in a professional activity causing static tension of the muscles, and detection of jammed muscles for the purpose of physical treatment like massage, or even as tools and devices among other tools and devices aiding to diagnose and/or treat a disease related to muscles. Methods for the determination of the state of tiredness of a muscle are also presented and claimed. It is to be noted, however, that the tiredness or tension of a muscle is not a disease. Therefore, diagnostic or therapeutic methods are not a target of the present application. The different embodiments may also be used for determining the properties of the muscle e.g. related to the relative proportions of different types of motor units in the given muscle due to the different motor units producing different frequencies. The embodiments may also be applicable to the detection of muscle properties in certain states such as multiple sclerosis (MS), myalgia or Parkinson's disease, since the frequencies produced by muscles in these states may be different.

A muscle consists of motor units, as explained earlier. These motor units may be individually innervated so that an order to contract may be delivered individually to the motor units. Some of the motor units, e.g. the smaller and slower ones, may be more easily activated than other motor units. Each type of motor unit has its characteristic frequency range produced by the electrical activity of the motor unit. The activity of the slow, fatigue resistant muscles is at lower frequency than the activity of the fast, easily fatigued muscles. Depending on the type of work and the condition of the muscle, different motor units may be activated. The electrical activation of the muscle cells causes them to contract, and they carry out work. Furthermore, also in the resting state of the muscle, some motor units are sporadically activated and such a pattern of activation causes a so-called resting tonus of the muscle. In other words, even a resting muscle is not completely passive, but has a small amount of constant activity happening. The contraction and the stable length of the muscle is in part controlled and maintained by so-called muscle spindles that are units that sense the elongation and pressure in a muscle and are this able to act as feedback units in the muscle-nerve system. Muscle spindles may also cause contraction of the muscle cells. Underlying the mechanical activation of the muscle is an electrical excitation taking place in the muscle cells.

The propagation of the electrical excitation of a muscle creates a varying electric potential that is measurable from the body surface by means of electrodes and a voltage measurement device suitable for measuring such signals. Such a signal may be called an electromyogram (EMG). The EMG signals from a resting muscle picked up from the body surface between two electrodes may be of the order of some microvolts or tens of microvolts, e.g. 5-20 µV, by their amplitude.

The rest EMG signals contain also smaller fluctuations of the order of 1 µV or less. From a working and moving muscle, the EMG signals may be significantly larger.

The motor units have different sizes in terms of length and thickness. The electrical excitation in a muscle cell bundle may have a different propagation speed and frequency range produced by the activation depending on the thickness (diameter) of the bundle—e.g. the thicker the bundler, the faster the propagation speed. Furthermore, the rate of rise of the excitation of the muscle bundle, i.e. the rate of change in the voltage across the cell membranes in the bundle, may vary according to the diameter of the bundle and/or the rate of rise of the excitation. The voltage signal picked up by the electrodes may therefore be different depending on which muscle cell bundles are excited. If fast muscle cell bundles with a large diameter are excited together with slower and smaller muscle cell bundles, such as in a non-tired normal muscle, the frequency content of the signal picked up by the electrodes contains a normal, wide frequency distribution. According to existing knowledge, it is known that when a muscle is exercised and it gets tired the signal at rest consists predominantly of lower frequencies. This may be due to the fast muscle cell bundles with higher frequency activity get tired more rapidly.

In the invention, it has been realized that the status a muscle that is not only mildly tired but passive involuntary tension may be detected by determining the high frequency content of the signal that the muscle creates at rest. This is in contrary to what is commonly understood of muscle signal analysis. In the invention, a method and devices have been created where the muscle signal is acquired with the help of electrodes, and a deviation in the frequency content of the signal towards the higher frequencies is used as an indicator for a passive involuntary tension state of the muscle. The degree of tiredness may also be detected by comparing the frequency content at the low frequencies, at the normal frequencies and at the high frequencies. Furthermore, spectral analysis may also be used to estimate the endogenous properties and motor unit composition of the muscle due to the different frequencies these motor units produce. This may comprise measurements from both active and resting muscle. The different devices that may employ the invention comprise, without limiting to these examples, at least a hand-held or movable muscle analyzer, a portable exercise computer, a wireless sensor attached to or implantable into the body, a physiological monitoring system for pilots embodied in a suit, an intelligent garment, a chair or another piece of furniture, and a treatment bed e.g. to be used in giving massage.

Figure 1:
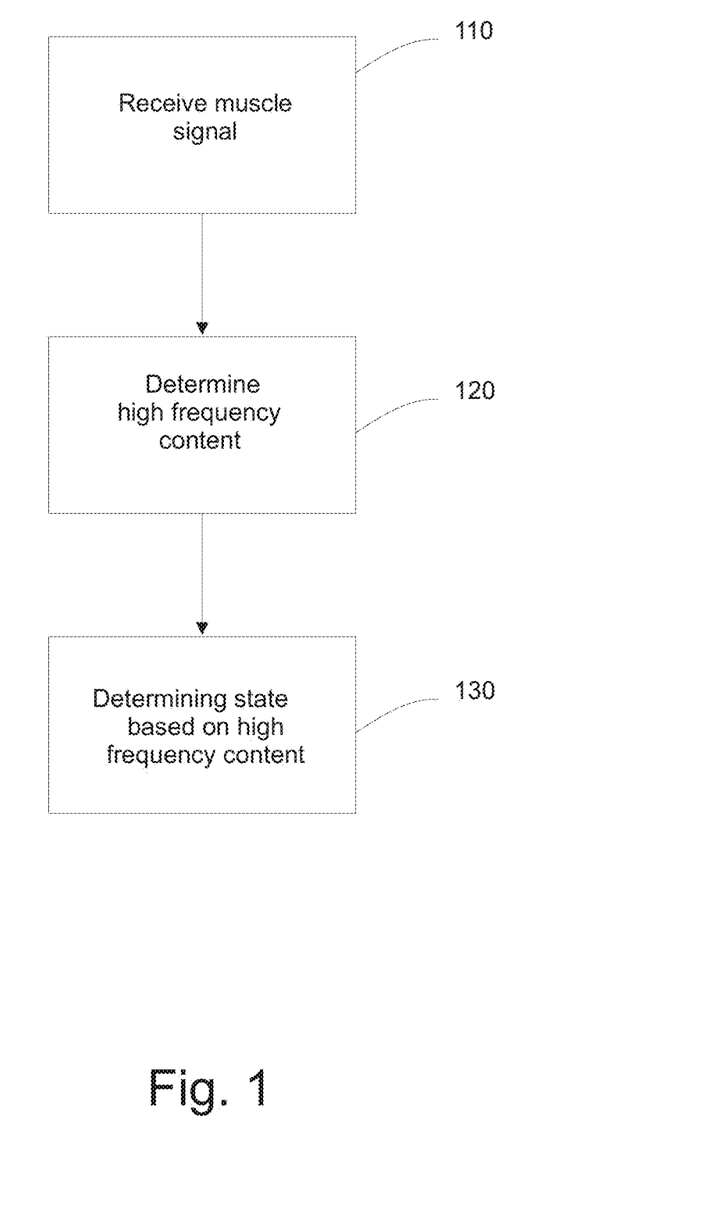
FIG. 1 shows a flow chart of a method for analyzing muscle signals to determine a muscle state.

FIG. 1 shows a flow chart of a method for analyzing muscle signals to determine a muscle state. In step 110, a signal measured from a muscle is received. The signal may have been measured e.g. with the help of electrodes or sensors sensing the magnetic field, or otherwise in a way that the signal is indicative of the electrical activity in the muscle. The signal may then be converted to digital format e.g. by analog-to-digital conversion, or the signal may be directly acquired in digital format. The signal is then e.g. stored in a memory, transmitted along an electric, optical or wireless connection or otherwise brought to be accessible for analysis.

At phase 120, the frequency content of the muscle signal is determined. The frequency content may be determined e.g. by performing a transform such as a Fourier transform, a fast Fourier transform, a discrete cosine transform, a wavelet transform or any other suitable transform. The transform may be used to convert the signal from time domain to frequency domain. Alternatively, the conversion may be omitted, and coefficients and results of the whole or partial transform may be used as input to a method for determining a high frequency content of the signal. The frequency information of the signal may be further processed e.g. by determining the energy and/or amplitude at different frequency bands such as 8-30 Hz (low frequency band), 20-60 Hz (normal frequency band) and 50-150 Hz (high frequency band). For some applications, the low-frequency band may start from as low as 0.5 Hz or lower and end as high as 40-50 Hz or higher. The middle band may start from 30-40 Hz and end at 50-80 Hz. The high-frequency band may start from 40-70 Hz and end at 100 Hz, 200 Hz, 300 Hz or higher. The bands may overlap, or there may be gaps between the bands. Alternatively, or in addition, the frequency content may be characterized by computing a number associated with different moments of the signal, as explained in the context of FIG. 2. A high moment number may be indicative of a frequency content at higher frequencies. The signal may also be analysed in time-domain, e.g. by zero-crossing analysis or by measuring peak-to-peak times from the signal (the smaller the time, the higher the frequency) For any of the analysis methods, the signal may be pre-processed before analysis, for example filtered and/or the signal may be scaled and/or normalized or the analysis results may be scaled and/or normalized. The signal may be processed so that higher and lower frequencies change place or are otherwise altered. The detection of characteristics of the original signal relating to the normal, tired and passive involuntary tension state may take place from such a processed signal.

At phase 130, the detected frequency content is used to determine the state of the muscle. If frequencies at a middle area are detected, or the frequency distribution resembles that of a signal from a non-tired normal muscle at rest, the muscle may be determined to be in the non-tired state. If low frequencies are detected, the muscle may be determined to be in the mildly tired state. If high frequencies compared to the non-tired muscle are detected, the muscle may be determined to be in a passive unvoluntary tension state. The result of the determination may then be indicated to a user. It may also be feasible to indicate the level of tiredness to a user. Alternatively or in addition, a threshold may be set beyond which a passive involuntary tension state of the muscle is indicated.

Figure 2:
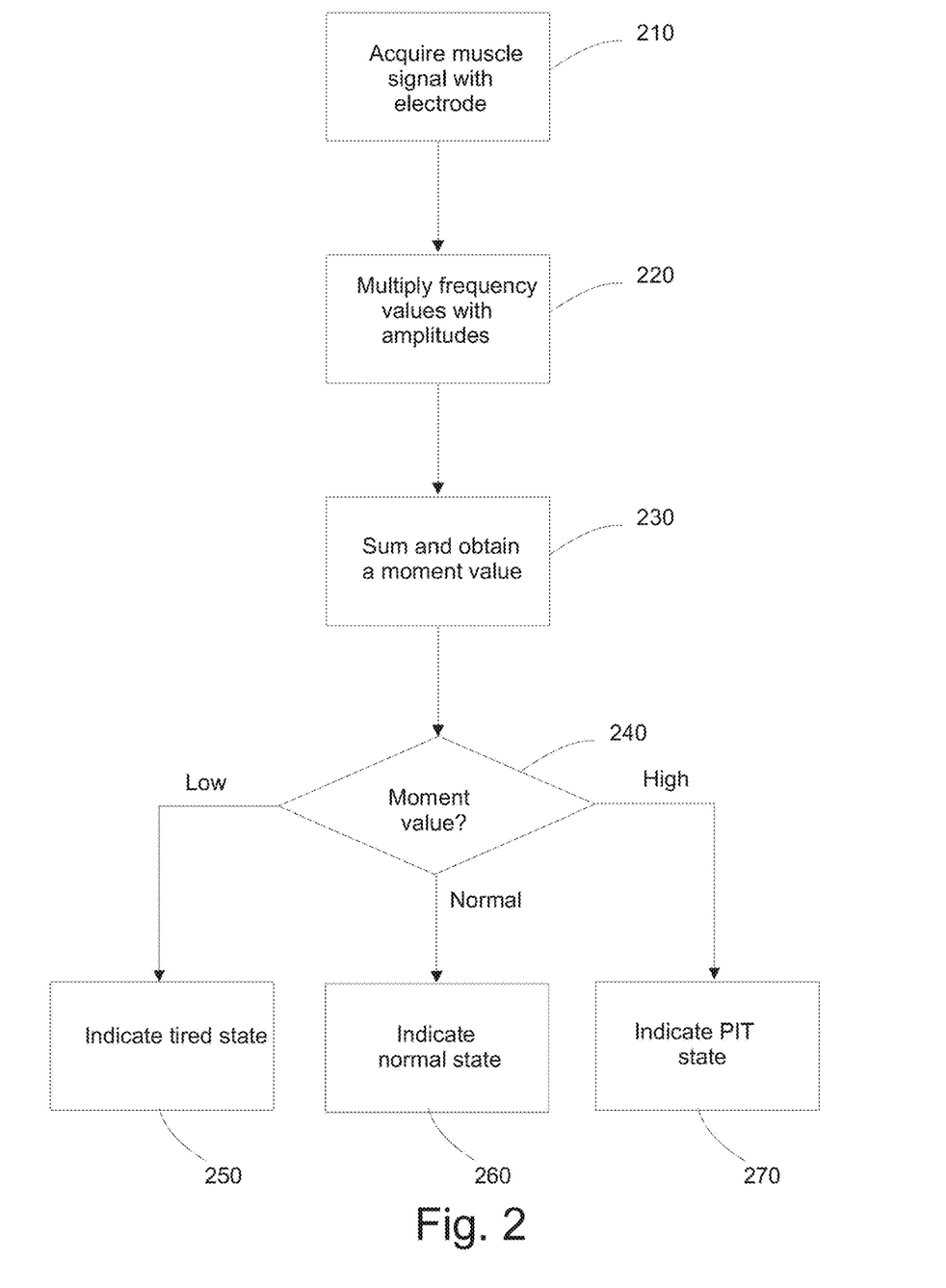
FIG. 2 shows a flow chart of a method for determining the spectral content of a muscle signal.
Figure 6A:
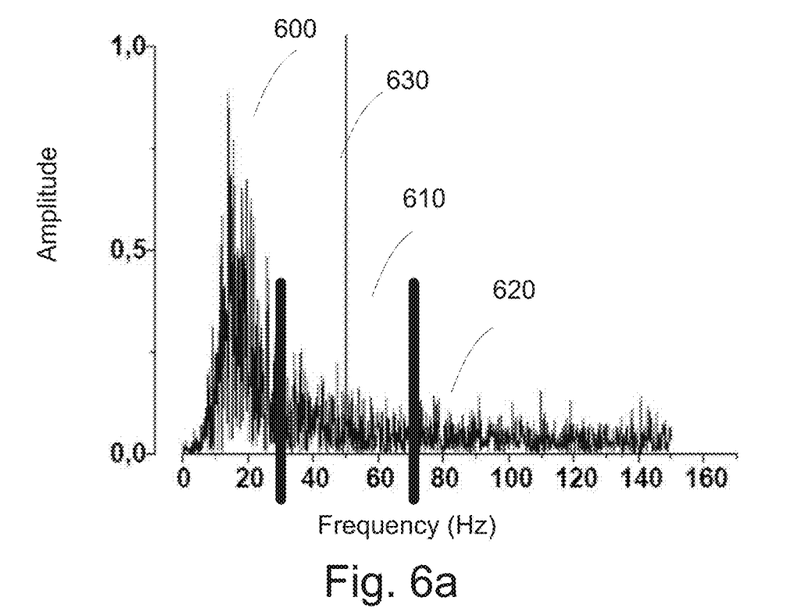
FIG. 6a shows a spectrum of a signal from a muscle in a non-tired normal state.

FIG. 2 shows a flow chart of a method for determining the spectral content of a muscle signal. In step 210, the signal from the muscle may be acquired e.g. with an electrode setup such as shown in FIGS. 3a to 3f. As explained earlier, the signal is converted to digital format for analysis. The signal may then be analyzed e.g. by Fourier transform, as also explained earlier. This may result in a spectrum such as shown in FIG. 6a, where amplitude (a) values according to frequency (f) are shown.

In step 220, the frequency values f may be multiplied with amplitude values a or otherwise combined. This may happen so that the frequency and amplitude values are formed into vectors so that the vector f comprises elements $(f_1, f_2 \ldots, f_n)$ where n is the number of spectral bins and the vector a comprises elements $(a_1, a_2 \ldots, a_n)$. The corresponding elements in the vectors are then multiplied, and summed together in step 230 to obtain a moment value or a spectral sum ss as an inner product of the vectors f and a according to formula ss=f·a. In the case presented above, the spectral sum is the first moment of the signal spectrum, and describes the location of the center of weight along the frequency axis. In other words, if the signal contains low frequencies, the spectral sum or the first moment have a small value, and if the signal contains high frequencies, they have a large value.

In step 240, the moment value or the spectral sum is evaluated e.g. against thresholds or by some other decision making method. If the signal is determined to have low frequencies (the spectral sum is small) compared to a signal from a normal non-tired muscle, a slightly tired muscle state is indicated in step 250. If the signal is determined to have medium frequencies (the spectral sum is of medium value), a non-tired muscle state is indicated in step 260. If the signal is determined to contain more high frequencies than a signal a normal non-tired muscle (high value of the spectral sum), a passive involuntary tension state of the muscle is indicated in step 270.

Figures 3A, 3B, 3C, 3D:
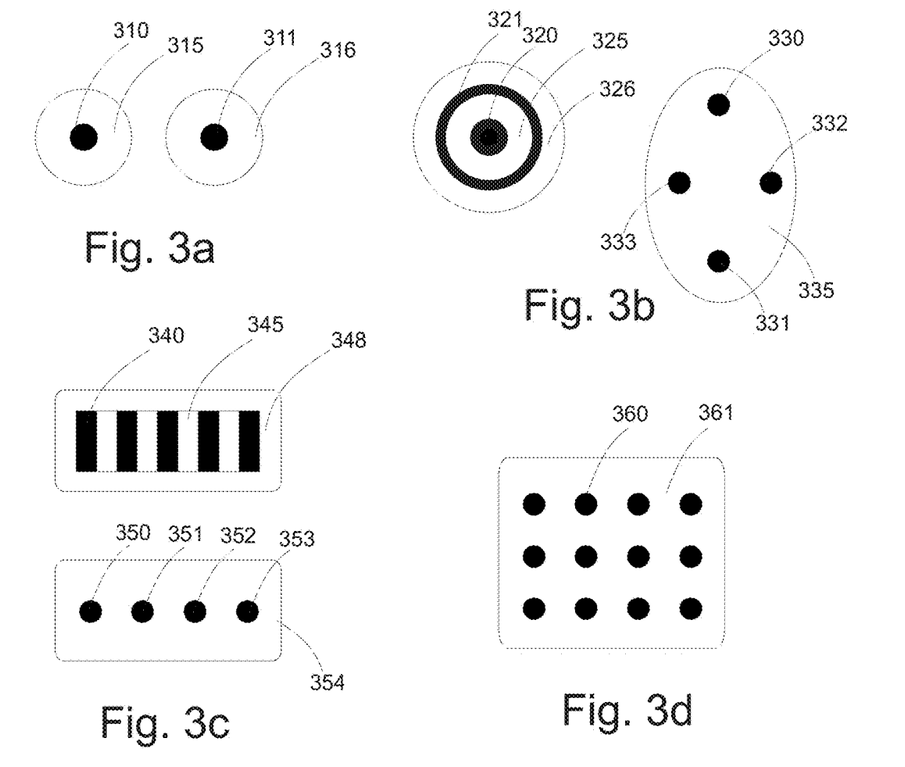
FIGS. 3a, 3b, 3c, 3d, 3e and 3f show different electrode arrangements for measuring a muscle signal: an electrode pair, a circular and a cross electrode, two different types of linear electrodes, an electrode array, and electrode arrangements with a surrounding

FIGS. 3a, 3b, 3c, 3d, 3e and 3f show different electrode arrangements for measuring a muscle signal. In FIG. 3a, an electrode pair is shown. The electrode pair may be a fixed pair so that the distance between electrodes 310 and 311 stays the same when the electrode pair is applied to the skin, or it may consist of two separate electrodes. The electrodes may be surrounded by electrical insulators 315 and 316 such as plastic, glass, porcelain, or air. In the case of air, the electrode may be essentially without any solid state insulator. The electrodes may be pieces of conducting material such as metal, semiconductor, carbon, conducting plastic or a composite material such as silver/silver-chloride mixture. The electrodes may be circular, rectangular, symmetric or asymmetric, or round or elongated in shape. The insulators 315 and 316 may be common to both electrodes, i.e. be physically the same object or two objects connected to each other, or they may be separate. What has been said about the materials and setup of the electrodes in case of an electrode pair may apply mutatis mutandis to other setups illustrated in FIGS. 3b to 3e. The shape of the lead field of an electrode pair such as in FIG. 3a is such that the electrode pair essentially picks a signal from the muscle at the same depth as the distance between the electrodes 310 and 311. The sensitivity of an electrode pair may therefore be tuned to different depths by altering the distance between the electrodes.

FIG. 3b displays two planar electrode setups. The electrodes 320 and 321 are concentric and pick up essentially a so-called Laplacian signal, i.e. a derivative signal of the one picked up by an electrode pair. The Laplacian electrode may be sensitive to signal sources below the electrode. Again, the electrodes may be separated and/or surrounded by insulators 325 and 326. In another setup, there are four electrodes 330, 331, 332 and 333 making up e.g. two electrode pairs in a cross-form setting. The electrodes 330 and 331 may be spaced apart by a different distance than the electrodes 332 and 333. Again, the electrodes may be surrounded by an insulator 335.

FIG. 3c displays two linear electrode setups. The electrodes 340 are arranged in a row with an insulator 345 between each two electrodes. There may be any number of electrodes, such as 3, 5, 7, or 10, or even a very high number like 50 or 100 in the linear strip of electrodes. The linear electrode arrangement may be surrounded by an insulator 348, where the insulator 348 may be of the same material as and in connection with the insulator 345, or it may be different material. The electrodes 350, 351, 352 and 353 are also arranged along a line, and they may be surrounded by a common insulator 355.

FIG. 3d displays an array of electrodes. The electrodes 360 may be arranged in a regular or irregular shape, for example in a grid of N by M electrodes, or electrodes being distributed randomly, or in a hexagonal setting. The electrodes may be surrounded by a common insulator 361.

Figure 3E:
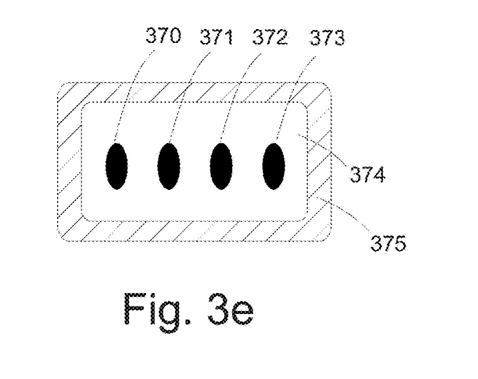
Figure 3F:
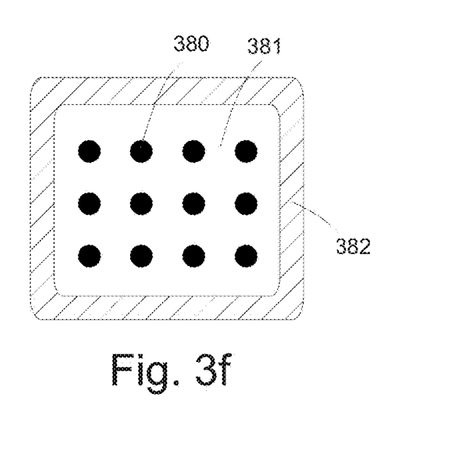

FIG. 3e displays a linear electrode arrangement surrounded by a ground body or element. The electrodes 370, 371, 372 and 373 may be arranged linearly, and they may be elongated in shape such that the elongation of the electrodes is perpendicular to the line along which the electrodes are arranged. The electrodes may be surrounded by an insulator 374. In the setup of FIG. 3e, there is a ground body or ground element 375 at least partially or completely surrounding the setup. The term surrounding may be understood loosely so that the ground body merely extends away from the set of electrodes, and is, for example, placed on at least two opposite sides of the electrodes. The ground body may not be an active member in the signal acquisition, and the ground body may be merely a large conducting object without any active elements or without being connected to the acquisition electronics in any way. The ground body may also extend in the depth dimension so that it forms a box open from one side around the electrodes (the box may have a passage for the electrode wires). The ground body may work to restrict the lead field of the electrode arrangement so that it even more precisely picks up signals below the arrangement and is insensitive to signals coming from the side. In addition, the ground element may protect the electrodes from picking up ambient electromagnetic noise. The ground element may also surround any other electrode setup such as the electrode array, as shown in FIG. 3f, where the electrodes 380 are surrounded by an insulator 381 and a ground element 382.

Figure 4A:
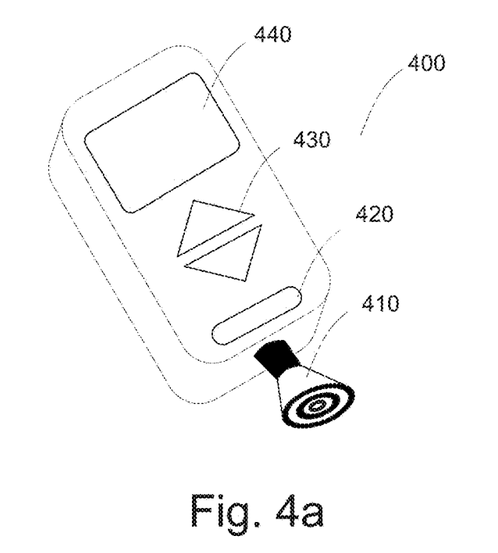
FIGS. 4a and 4b show a hand-held muscle signal analyzer and electrode heads for the same.

FIG. 4a shows a hand-held muscle signal analyzer 400. The apparatus has an electrode head 410 that may be attached and disconnected from the apparatus as needed. This arrangement enables the electrode arrangement to be changed as needed, for example by type of muscle to be analyzed. Electrode arrangements with deeper sensitivities may be used with deeper and/or larger muscles, and there may be electrode heads suitable for even and uneven or curving skin surfaces. The different electrode heads may have different material. Further, the electrode heads may be personal or they may be single-use to improve hygienity. The apparatus may also comprise buttons for controlling the operations, for example an acquisition button 420 and user interface control buttons 430. There may be a display or a led indicator 440, or a speaker for emitting a sound for the purpose of showing to the user the result of the muscle state analysis.

Figure 4B:
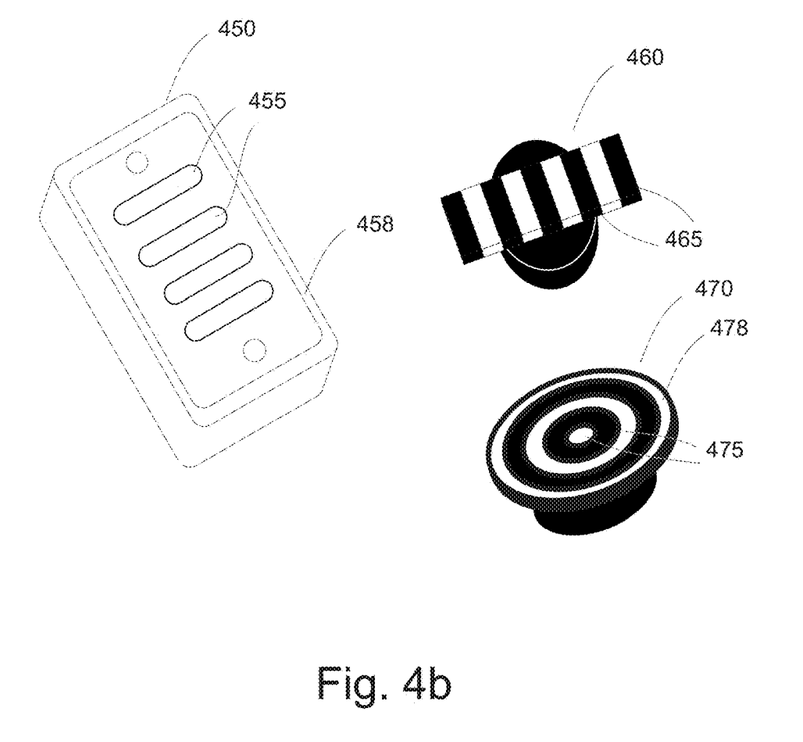

FIG. 4b shows electrode heads for a hand-held muscle signal analyzer. The electrode head 450 is of a linear type where the electrodes 455 are arranged in a linear manner. The electrodes 455 may be elongated in shape, and to improve contact, they may be slightly elevated above the insulating material surrounding them. The casing 458 of the electrode head 450 acts as a grounding body and it makes contact with the skin, as well. The electrode head 460 is a different type of a linear electrode with the electrodes 465 being separated by insulating elements. The electrode head 470 is of the circular type where the electrodes 475 are concentric. The electrode head has a grounding body 478. All of the electrode heads have a connector for physically and/or electrically connecting the head to the analyzer. The electrode heads may be passive, or they may be active so that they contain acquisition electronics for amplifying and/or digitizing the signal picked up by the electrodes.

Figure 5A:
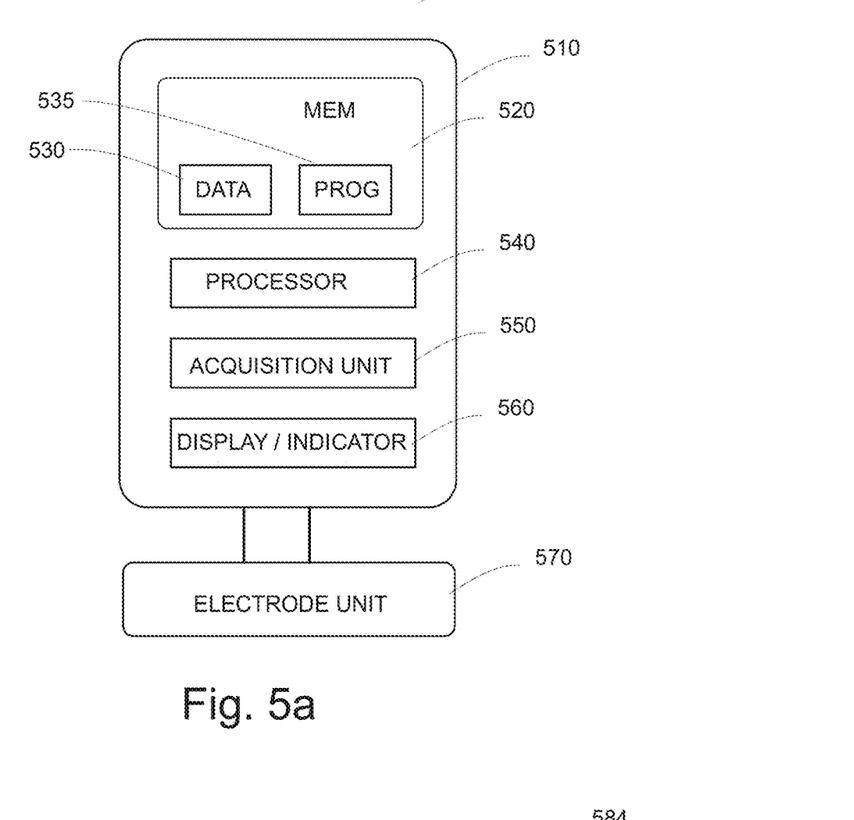
FIG. 5a shows a block diagram of an apparatus for determining the state of a muscle.

FIG. 5a shows a block diagram of an apparatus 500 for determining the state of a muscle. The apparatus may be embodied in a casing 510 suitable for holding the apparatus by hand for carrying out the acquisition of the muscle signals. The apparatus may have memory 520 for holding data 530 such as the acquired signal and programs 535 such as the frequency content analysis program and/or the acquisition control program and/or the user interface program. The apparatus may have an acquisition unit 550 for amplifying and/or digitizing the signal picked up by the electrode unit 570. The functionality of the acquisition unit may also be partly or completely implemented in the electrode unit. There may also be a display or indicator unit for showing or indicating the result of the analysis to a user. The apparatus may function so that the acquisition and indication is done in a one-shot manner, or so that the acquisition, analysis and indication happens continuously, thereby allowing the apparatus to be moved along the skin to detect the areas in the muscles that are in the passive involuntary tension state. The apparatus may indicate the passive involuntary tension state by a sound or a light signal.

Figure 5B:
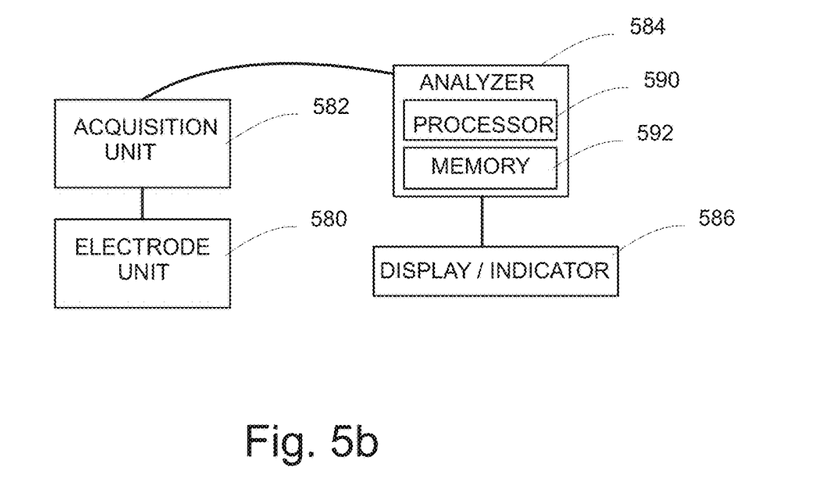
FIG. 5b shows a block diagram of a system for determining the state of a muscle.

FIG. 5b shows a block diagram of a system for determining the state of a muscle. The system may have an electrode unit 580, an acquisition unit 582, an analysis unit 584 comprising a processor 590 and memory 592, and a display/indicator unit 586. The various units may have various degree of functionality, e.g. they may contain circuitry, processors, memory and communication means in addition to their basic functionality. The different units may be implemented as separate devices, or some or all of them may be combined in the same device. In addition, the different units and devices may be connected to each other via a wired, optical or wireless connection for transferring signals, commands and data.

FIG. 6a shows an example spectrum of a signal from a muscle in a non-tired normal state. The spectrum shows relatively high content of low frequencies 600 in the signal, and a clear content of medium frequencies 610. The high frequencies 620 are clearly lower in the signal acquired from a normal non-tired muscle at rest. The spectrum also shows the 50 Hz ambient electrical noise 630 picked up by the acquisition unit.

Figure 6B:
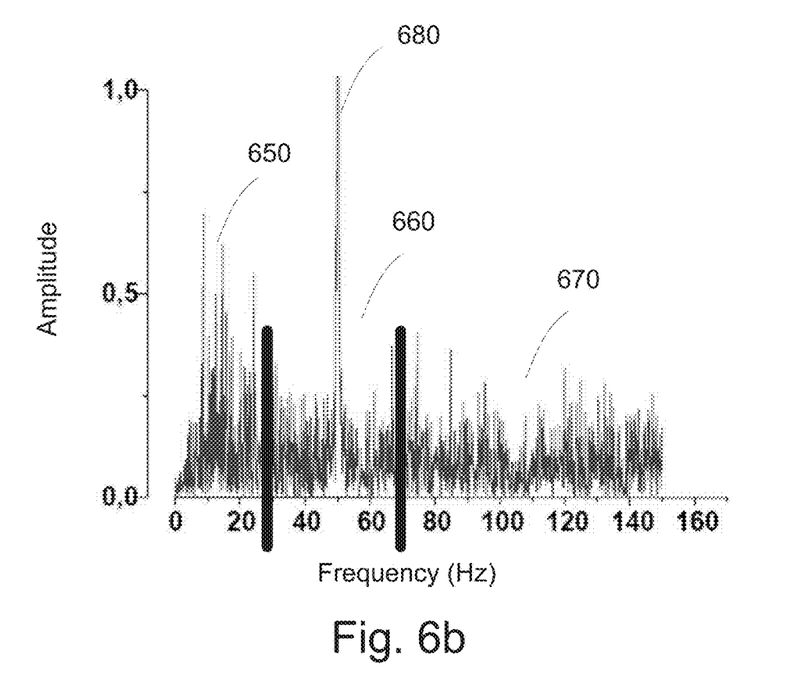
FIG. 6b shows a spectrum of a signal from a passive involuntary tension muscle.

FIG. 6b shows an example spectrum of a signal from a passive involuntary tension muscle. Compared to the spectrum of FIG. 6a, the low frequency content 650 of the signal from a passive involuntary tension muscle is lower than for a non-tired muscle. This is contrary to what is conventionally understood of the behavior of muscle signals. The medium frequency content 660 of the signal from a passive involuntary tension muscle shows some increase compared to a non-tired muscle. There is a clear increase in the high frequency content 670 of the signal from a passive involuntary tension muscle compared to a non-tired muscle. Correspondingly, the normalized spectral sum indicator for the passive involuntary tension muscle is higher compared to the non-tired muscle. The ambient 50 Hz noise 680 is again present.

The various embodiments of the invention can be implemented with the help of computer program code that resides in a memory and causes the relevant apparatuses to carry out the invention. For example, a hand-held analysis device may comprise circuitry and electronics for acquiring, receiving and analyzing data, computer program code in a memory, and a processor that, when running the computer program code, causes the device to carry out the features of an embodiment. Yet further, a separate analysis device may comprise circuitry and electronics for handling, receiving and transmitting data, computer program code in a memory, and a processor that, when running the computer program code, causes the device to carry out the features of an embodiment.

It is obvious that the present invention is not limited solely to the above-presented embodiments, but it can be modified within the scope of the appended claims.

The invention claimed is:

1. A method for analyzing muscle signals acquired by a hand-held muscle signal apparatus, the hand held muscle signal apparatus comprising a processor and an electrode head comprising at least one electrode pair coupled to the processor, wherein a distance between electrodes of the at least one electrode pair, when the at least one electrode pair is disposed on a skin surface proximate a top of a muscle during a resting state of said muscle, determines a depth from which the at least one electrode pair is configured to detect said muscle signals, the at least one electrode pair disposed on the skin surface being surrounded by a ground body, said ground body configured to restrict a pick-up of signals by the at least one electrode pair to signals below the at least one electrode pair and within a perimeter of the ground body, the method comprising:

the at least one electrode pair of the hand-held muscle signal apparatus acquiring a signal from said muscle:

the processor determining a measure indicative of a frequency content of said acquired signal, wherein said determining by the processor comprises:

determining a moment value of a spectrum of said acquired signal, wherein said moment value is a measure determined by multiplying a frequency value of a frequency bin of frequencies of the frequency content of the acquired signal with an amplitude value of the frequency bin to form a bin product and summing bin products for different frequencies, and wherein said moment value corresponds to the frequency content of said acquired signal;

and wherein the processor is further configured to determine that the muscle is in a non-tired state when said moment value has a first value, determine that the muscle is in a tired state when said moment value has a second value, the second value being lower than the first value, and determine that the muscle is in a passive involuntary tension state when said moment value has a third value, the third value being higher than the first value; and wherein the method further comprises:

moving at least one electrode pair of said hand-held muscle signal apparatus to at least one other muscle area to acquire at least one other signal during a resting state of the at least one other muscle area, determining, by the processor, a measure indicative of a frequency content of said acquired at least one other signal, determining, by the processor, a moment value of a spectrum of the acquired at least one other signal wherein the moment value of the spectrum of the acquired at least one other signal is a measure determined by multiplying a frequency value of a frequency bin of frequencies of the frequency content of the acquired at least one other signal with an amplitude value of the frequency bin to form a bin product and summing bin products for different frequencies, and wherein said moment value of the spectrum of the acquired at least one other signal corresponds to the frequency content of the acquired at least one other signal;

determining, by the processor, that the at least one other muscle area is in a tired state, the non-tired state or the passive involuntary tension state based on the determined moment value; and indicating on the display of the hand-held muscle signal apparatus the state of the muscle and the at least one other muscle area, wherein the at least one other signal is acquired in a continuous manner.

2. The method according to claim 1, wherein the processor is further configured to indicate on an indicator unit whether the muscle is in the non-tired, tired or passive involuntary tension state.

3. The method according to claim 1, wherein the processor is further configured to indicate the passive involuntary tension state by a sound or light signal outputted on an indicator unit.

4. A hand-held muscle signal apparatus for determining a state of a muscle, the hand held muscle signal apparatus comprising an electrode head comprising at least one electrode pair wherein a distance between electrodes of said at least one electrode pair is arranged such that said distance determines a depth from which the at least one electrode pair picks up a muscle signal from the muscle, the at least one electrode pair being surrounded by a ground body, said ground body configured to restrict a detection of signals by the at least one electrode pair to signals below the at least one electrode pair and within a perimeter of the ground body, the apparatus comprising a processor and a memory including computer program code, the computer program code, when executed by the processor, causing the apparatus to:

receive a muscle signal with the at least one electrode pair of the hand-held muscle signal apparatus, the signal having been measured from the muscle in a resting state, determine a measure indicative of a frequency content of said measured signal, said determining comprising:

determining a moment value of a spectrum of said measured signal, wherein said moment value is a measure determined by multiplying a frequency value of a frequency bin of frequencies of the frequency content of the measured signal with an amplitude value of the frequency bin to form a bin product and summing bin products for different frequencies, and wherein said moment value corresponds to the frequency content of said measured signal, determining whether said moment value has a first value, a second value or a third value, the second value being lower than the first value and the third value being higher than the first value;

determining that the muscle is in a non-tired state when said moment value has the first value, determining that the muscle is in a tired state when said moment value has the second value, and determining that the muscle is in a passive involuntary tension state when said moment value has the third value; and wherein the computer program code, when executed by the processor is configured to cause the hand-held muscle signal apparatus to:

acquire at least one other signal from at least one other muscle area during a resting state of the at least one other muscle area using at least one electrode pair of the hand-held muscle signal apparatus moved to at least one other muscle area;

determine a measure indicative of a frequency content of said at least one other signal, determine a moment value of a spectrum of the at least one other signal, wherein the moment value of the spectrum of the at least one other signal is a measure determined by multiplying a frequency value of a frequency bin of frequencies of the frequency content of the at least one other signal with an amplitude value of the frequency bin to form a bin product and summing bin products for different frequencies, and wherein said moment value of the spectrum of the at least one other signal corresponds to the frequency content of the at least one other signal; and determine that the at least one other muscle area is in a tired state, the non-tired state or the passive involuntary tension state based on the determined moment value;

wherein the hand-held muscle signal apparatus is configured to provide an indication on the display of the hand-held muscle signal apparatus of the determined state of the at least one other muscle area and the at least one other signal is acquired in a continuous manner.

5. An apparatus according to claim 4, comprising:
an electrode arrangement comprising:
more than two electrodes of conducting material configured to make contact with a skin surface proximate the muscle when said electrode arrangement is operated, said at least more than two electrodes arranged in a row with an insulator between each of the more than two electrodes;
an electrical insulator surrounding at least one of said more than two electrodes, and
a passive ground body of a conducting material configured to make contact with the skin surface when said electrode arrangement is operated, said ground body surrounding said at least two electrodes of the more than two electrodes to limit said more than two electrodes from picking up a signal propagating on the skin surface from outside an extent of said ground body.

6. An apparatus according to claim 5, further comprising:
the processor for processing said signal measured from the muscle, and
an indicator on a user interface of the apparatus configured to provide an indication that the muscle is in the passive involuntary tension state based on the moment value having the high value.

7. An apparatus according to claim 5, wherein said electrode arrangement comprises at least two pairs of electrodes, and wherein a distance between different electrodes in said at least two pairs of electrodes is varied to create a different depth sensitivity for the said at least two pairs of electrodes.

8. An apparatus according to claim 7, wherein said at least two pairs of electrodes are arranged in either a linear arrangement essentially along one line or in a crossed setting such that lines between electrodes in the electrode pairs form a straight angle cross.

9. The apparatus according to claim 4, the apparatus further comprising an indicator unit, wherein the processor is further configured to indicate on the indicator unit whether the muscle is in the non-tired, tired or passive involuntary tension state on the indicator unit, and wherein the indication of the passive involuntary tension state is by a sound or light signal outputted on the indicator unit.

10. A system for indicating a state of a muscle, the system comprising a hand-held muscle signal apparatus comprising an electrode head comprising an electrode arrangement, said electrode arrangement comprising at least one electrode pair coupled to a processor, wherein a distance between electrodes of said at least one electrode pair, when the at least one electrode pair is disposed on a skin surface proximate a top of a muscle during a resting state of said muscle, determines a depth from which the at least one electrode pair picks up muscle signals, the at least one electrode pair being surrounded by a ground body, said ground body configured to restrict a pick-up of said muscle signals by the at least one electrode pair to those muscle signals below the at least one electrode pair and within a perimeter of the ground body, the system further comprising a memory including computer program code, the computer program code, when executed by the processor, causing the system to:
acquire a signal from the top area of a muscle using the electrode arrangement,
determine a measure indicative of a frequency content of said signal, said determining comprising
determining a moment value of a spectrum of said signal, wherein said moment value is a measure determined by multiplying a frequency value of a frequency bin of frequencies of the frequency content of the signal with an amplitude value of the frequency bin to form a bin product and summing bin products for different frequencies, and wherein said moment value corresponds to the frequency content of said signal,
determining whether said moment value has a first value, a second value or a third value, the second value being lower than the first value and the third value being higher than the first value;
determining that the muscle is in a non-tired state when said moment value has the first value,
determining that the muscle is in a tired state when said moment value has the second value, and
determining that the muscle is in a passive involuntary tension state when said moment value has the third value; and wherein the computer program code, when executed by the processor is configured to cause the hand-held muscle signal apparatus to:
acquire at least one other signal during a resting state of at least one other muscle area using the electrode arrangement of the hand-held muscle signal apparatus moved to at least one other muscle area;
determine a measure indicative of a frequency content of said at least one other signal,
determine a moment value of a spectrum of the at least one other signal, wherein the moment value of the spectrum of the at least one other signal is a measure determined by multiplying a frequency value of a frequency bin of frequencies of the frequency content of the at least one other signal with an amplitude value of the frequency bin to form a bin product and summing bin products for different frequencies, and wherein the moment value of the spectrum of the at least one other signal corresponds to the frequency content of the at least one other signal, and
determine that the at least one other muscle area is in a tired state, the non-tired state or the passive involuntary tension state based on the determined moment value; wherein the hand-held muscle signal apparatus is configured to provide an indication on the display of the hand-held muscle signal apparatus of the determined state of the at least one other muscle area and the at least one other signal is acquired in a continuous manner.

11. A system according to claim 10, wherein said electrode arrangement comprises:
more than two electrodes of conducting material configured to make contact with a skin surface near the top of the muscle when said electrode arrangement is operated, said more than two electrodes arranged in a row with an insulator between each two electrodes of said more than two electrodes,
an electrical insulator surrounding at least one of said at least two electrodes, and
a passive ground body of a conducting material configured to make contact with the skin surface when said electrode arrangement is operated, said ground body surrounding said more than two electrodes to limit said more than two electrodes from picking up a signal on the skin surface from outside of an extent of said ground body.

12. A system according to claim 10, wherein said electrode arrangement comprises at least two pairs of electrodes, and said at least two pairs of electrodes have a different distance between the electrodes in the pair for creating a different depth sensitivity for the at least two pairs of electrodes.

13. A system according to claim 12, wherein said at least two pairs of electrodes are arranged in either a linear arrangement essentially along one line or in a crossed setting such that the electrodes in the electrode pairs are aligned along lines forming a straight angle cross.

14. The system according to claim 10, the system further comprising an indicator unit, wherein the processor is further configured to indicate on the indicator unit whether the muscle is in the non-tired, tired or passive involuntary tension state and wherein the indication of the passive involuntary tension state is by a sound or light signal outputted on the indicator unit.

15. A computer program product embodied on a non-transitory computer readable medium resident in at least one processor of a hand-held muscle signal apparatus or system, said hand-held muscle signal apparatus or system comprising an electrode head including an electrode arrangement, the computer program product comprising computer executable instructions that, when executed on the at least one processor of the hand-held muscle signal apparatus or system, cause the hand-held muscle signal apparatus or system to:
receive a signal, the signal having been measured from a top area of a muscle with the electrode arrangement comprising at least one electrode pair wherein a distance between electrodes of said at least one electrode pair determines a depth from which the at least one electrode pair picks up said muscle signals, the at least one electrode pair being surrounded by a ground body, said ground body configured to restrict a pick-up of said muscle signals by the at least one electrode pair to muscle signals below the at least one electrode pair and within a perimeter of the ground body, the muscle being in a resting state,
determine a frequency content of said signal, said determining comprising:
determining a moment value of a spectrum of said signal, wherein said moment value is a measure determined by multiplying a frequency value of a frequency bin of frequencies of the frequency content of the signal with an amplitude value of the frequency bin to form a bin product and summing bin products for different frequencies, and wherein said moment value corresponds to the frequency content of said signal,
determining whether said moment value has a first value, a second value or a third value, the second value being lower than the first value and the third value being higher than the first value;
determining that the muscle is in a non-tired state when said moment value has the first value,
determining that the muscle is in a tired state when said moment value has the second value, and
determining that the muscle is in a passive involuntary tension state when said moment value has the third value; wherein the computer instructions, when executed by the at least one processor of the hand-held muscle signal apparatus or system are further configured to cause the hand-held muscle signal apparatus or system to:
acquire at least one other signal during a resting state of the at least one other muscle area using at least one electrode pair of the hand held muscle signal apparatus moved to at least one other muscle area;
determine a measure indicative of a frequency content of the at least one other signal,
determine a moment value of a spectrum of the at least one other signal, wherein the moment value of the spectrum of the at least one other signal is a measure determined by multiplying a frequency value of a frequency bin of frequencies of the frequency content of the at least one other signal with an amplitude value of the frequency bin to form a bin product and summing bin products for different frequencies, and wherein the moment value of the spectrum of the at least one other signal corresponds to the frequency content of the at least one other signal; and
determine that the at least one other muscle area is in a tired state, the non-tired state or the passive involuntary tension state based on the determined moment value;
wherein the hand-held muscle signal apparatus is configured to provide an indication on the display of the hand-held muscle signal apparatus of the determined state of the muscle and at least one other muscle area and the at least one other signal is acquired in a continuous manner.

16. The computer program product according to claim 15, wherein the hand-held muscle signal apparatus or system is further configured to indicate on an indicator unit whether the muscle is in the non-tired, tired or passive involuntary tension state, and wherein the indication of the passive involuntary tension state is by a sound or light signal outputted on the indicator unit.

* * * * *